United States Patent [19]

Hetzel

[11] Patent Number: 5,059,122
[45] Date of Patent: Oct. 22, 1991

[54] DENTAL SCALER
[75] Inventor: Max Hetzel, Deitingen, Switzerland
[73] Assignee: Bien-Air S.A., Bienne/Biel, Switzerland
[21] Appl. No.: 358,339
[22] PCT Filed: Aug. 24, 1988
[86] PCT No.: PCT/CH88/00144
  § 371 Date: Apr. 25, 1989
  § 102(e) Date: Apr. 25, 1989
[87] PCT Pub. No.: WO89/01763
  PCT Pub. Date: Mar. 9, 1989
[30] Foreign Application Priority Data
  Aug. 25, 1987 [CH] Switzerland ............... 03259/87
[51] Int. Cl.[5] .................................. A61C 1/07
[52] U.S. Cl. ............................. 433/118; 433/119
[58] Field of Search .......................... 433/118, 119

[56] References Cited
U.S. PATENT DOCUMENTS

| Re. 28,752 | 3/1976 | Balamuth | 433/119 |
| 3,743,868 | 7/1973 | Kawada | 310/8.1 |
| 4,332,558 | 6/1982 | Lustig | 433/119 |

FOREIGN PATENT DOCUMENTS

| 2241189 | 3/1974 | Fed. Rep. of Germany | 433/119 |
| 8507777 | 6/1985 | Fed. Rep. of Germany | 433/119 |
| 620004 | 3/1949 | United Kingdom | 433/119 |
| 1394010 | 5/1975 | United Kingdom | 433/119 |

Primary Examiner—John J. Wilson
Attorney, Agent, or Firm—McGlew & Tuttle

[57] ABSTRACT

A dental scaler comprises a hollow sleeve and, arranged inside it, a vibrating piezoelectric transducer bearing a scraper, the extremity of which protrudes from the sleeve, and includes an amplifier connected to the transducerk. The transducer includes a base, of a series of piezoelectric chips on the surfaces of which are arranged electrodes connected in such a manner as to define an input and an output, and a head to which the scraper is coupled. The amplifier has an input, an output and two feeder terminals receiving a low direct voltage by way of a cable connected to an external source of voltage. The output and input of the transducer are connected, respectively, to the input and the output of the amplifier to form an oscillator, the frequency of which is determined by the resonant frequency of the transducer coupled to the scraper.

8 Claims, 3 Drawing Sheets

DENTAL SCALER

BACKGROUND OF THE INVENTION

1. Field of the Invention

The present invention relates in general to dentistry and, in particular, to a new and useful electrical device used in dentistry to remove tartar found on the teeth.

2. Background of the Invention

Similar devices are known, generally under the name of dental scalers, they facilitate the work of the dental practitioner and they are in current use in dentists' offices. These devices appear in the form of a cylindrical sleeve that can be held in the hand and comprising, at one extremity, a flexible electrical cable and, at the other extremity, a vibrating scraper. When the scraper is put in contact with the tartar, its rapid movements permit it to fissure the tartar and to detach it easily from the tooth on which it has been deposited.

In an embodiment that is marketed, the scraper is mounted on a vibrating piezoelectric transducer arranged inside the sleeve. The transducer comprises electrodes connected to the cable which, in turn, is connected to a source of alternating current supplying electric energy to the device. This alternating current is applied to the transducer and it has the effect of putting it into forced vibration. To obtain the best yield from the conversion of the electric energy supplied by the source into mechanical energy available at the extremity of the scraper, the current frequency must be equal to the fundamental resonant frequency of the transducer connected to the scraper, which is about 50 kHz. The amplitude of motion of the scraper is determined, in turn, by the amplitude of the voltage and, in order to be able to work under good conditions, this voltage should be on the order of 600 volts.

In use, such a device presents two principal disadvantages: The contact of the scraper with the tooth has the effect of modifying the resonant frequency of the transducer to which it is attached. Since the output of the transducer is reduced under these conditions, the voltage applied to the electrodes must be increased in order to keep the amplitude of the scraper constant. The thermal dissipation of the transducer can then become considerable and render the sleeve disagreeable to hold in one's hand.

Also, since the transducer has to be supplied with high tension current, about 600 volts, there is a risk of electrocution for both the patient and the physician, if the cable is badly insulated. To reduce this risk, the cable must have good insulation, to wit, a thick one. This has the effect of reducing the flexibility of the cable, rendering the movement of the sleeve difficult, yet without totally reducing the danger resulting from the wear and tear of the insulation in places where the cable is under greatest stress.

SUMMARY OF THE INVENTION

The present invention provides a dental scaler that does not exhibit the disadvantages of the prior art. The scaler according to the invention is comprises of a hollow sleeve that can be held by hand and, arranged inside this sleeve there is a vibrating piezoelectric transducer having an electric input and outlet and exhibits a node and antinode of motion. A scraper is connected to the transducer in the spot of the antinode of motion, with a part of the scraper protruding from the sleeve. In addition, electric conductors are connected by means of a cable to an external source of current which also supplies the scaler with the electrical energy necessary for its operation.

A particularly remarkable feature of the invention is that the sleeve comprises additionally an electronic amplifier that has an input, an output, and two feeder terminals, with the input and output of the amplifier being connected respectively to the output and input of the transducer. Thus this circuit forms an oscillator. The transducer connected to the scraper plays the role of a resonator and the amplitude that of a maintenance circuit and the feeder terminals to the conductors to receive direct current.

It is an advantage of the invention that the basic resonant frequency of the transducer with the scraper determines the frequency of the oscillator. The transducer vibrates always at its resonant frequency and thus, under the best output conditions, even when this frequency is modified by the action of the scraper.

Another advantage results from the fact that the amplifier is supplied, by way of the cable with a low direct voltage, typically 24 volts, and thus presenting no danger.

Accordingly, it is an object of the invention to provide a dental scaler which includes a hollow sleeve can be held in one's hand and includes in its interior a vibrating piezoelectric transducer. It has an input and an output and exhibits a node and an antinode of motion, with a scraper being connected to the transducer at the antinode and which has a part which protrudes from the sleeve and which further includes electrical conductors for a cable connection at its end opposite to the scraper, the transducer being connected to the electrical conductor and having a transducer input and a transducer output with an electric amplifier having an amplifier input and an amplifier output and two feeder terminals, the amplifier input and amplifier output being respectively connected to the transducer output and the transducer input so as to form an oscillator, the transducer being connected to the scraper so as to form a resonator and the amplifier forming a maintenance circuit.

A further object of the invention is to provide a dental scaler which is simple in design, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which preferred embodiments of the invention are illustrated.

DETAILED DESCRIPTION OF THE DRAWINGS

Figure 1:
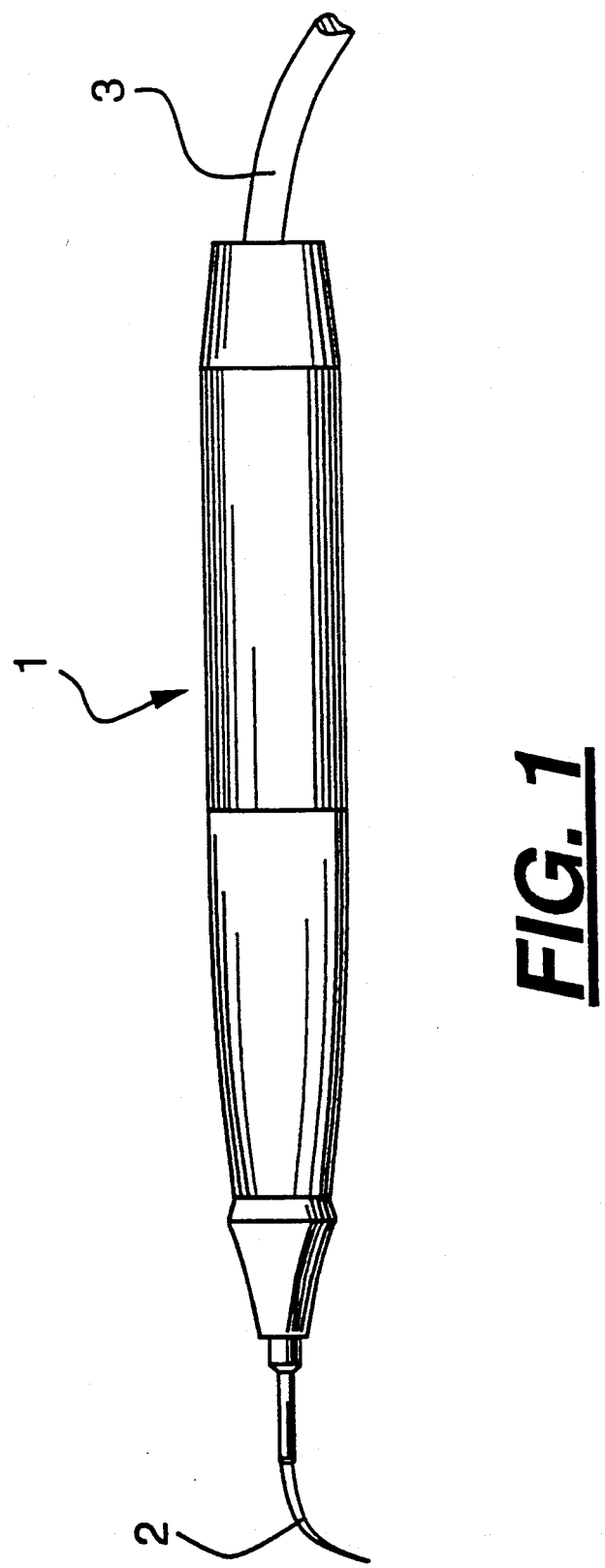
FIG. 1 is a side elevational view of an embodiment of the scaler according to the invention.

With reference to the drawings, and in particular to FIG. 1 an embodiment of the dental scaler according to the invention includes a hollow sleeve 1, which is substantially cylindrical and is typically 15 cm long and 2 cm in diameter, intended to be held in the hand of the treating physician. The sleeve 1 can advantageously be comprised of several cylindrical parts, assembled by being screwed together, with the separation of these parts permitting access to the interior parts.

A scraper 2, intended to remove the tartar deposited on a tooth protrudes from one end of the sleeve 1. An electric cable 3 is attached at the opposite extremity of the sleeve 1. This cable 3 comprises two conductors and it connects the sleeve 1 to a source of fixed current connected to the network, (not shown) supplying the scaler with electric energy necessary to put the scraper 2 in motion.

The connection of cable 3 to sleeve is preferentially effected by means of a universal connector of a known type, not shown, permitting the cable to be easily separated from the scaler. The same cable can thus also serve to supply a scaler which, for example, has a tip containing a cutter. It is possible, of course, also to joint to the cable, conduits for the transport of fluids, such as water, or air, with the universal connector providing the connection of these conduits to the corresponding conduits arranged in the sleeve and emerging near the scraper in such a manner that these fluids can reach the tooth.

Figure 2:
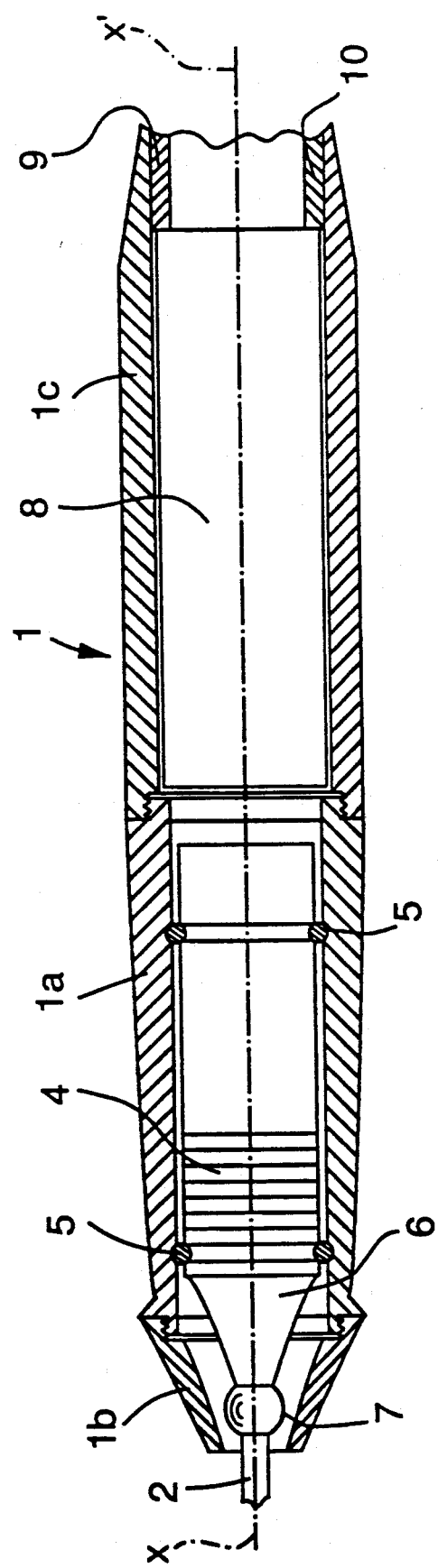
FIG. 2 is an enlarged sectional view showing the arrangement of the different constituents making up the scaler of FIG. 1.

FIG. 2 shows, in sectional view, the inside structure of the scaler. Sleeve 1 includes three hollow part, 1b, 1a and 1c, arranged one after the other, with part 1a in the center. Each part is screwed to the neighboring part, all together forming a hollow rotating body.

A piezoelectric transducer 4 is arranged inside the center part 1a of sleeve 1. It will be described in detail further on. This transducer has the shape of a long cylinder showing an axis of symmetry xx' which, in FIG. 2, coincides with the axis of revolution of the sleeve 1. Two elastic rings 5 provide the suspension of the transducer inside part 1a and they rest on circular grooves provided in the central side facing these two parts. Lastly, the active extremity of the transducer, that which corresponds to the antinode of motion, supports directly, or by way of coupling elements 6 and 7 to be described further on, the scraper 2 which exits from sleeve 1 through part 1b.

An electronic amplifier 8 is situated in part 1c. This amplifier contains an input, an outlet and two feeder terminals. The input and the output are connected to transducer 4 by connections that are not shown, while the feeder terminals are connected to two conductors 9 and 10 that are part of the universal connector.

Figure 3:
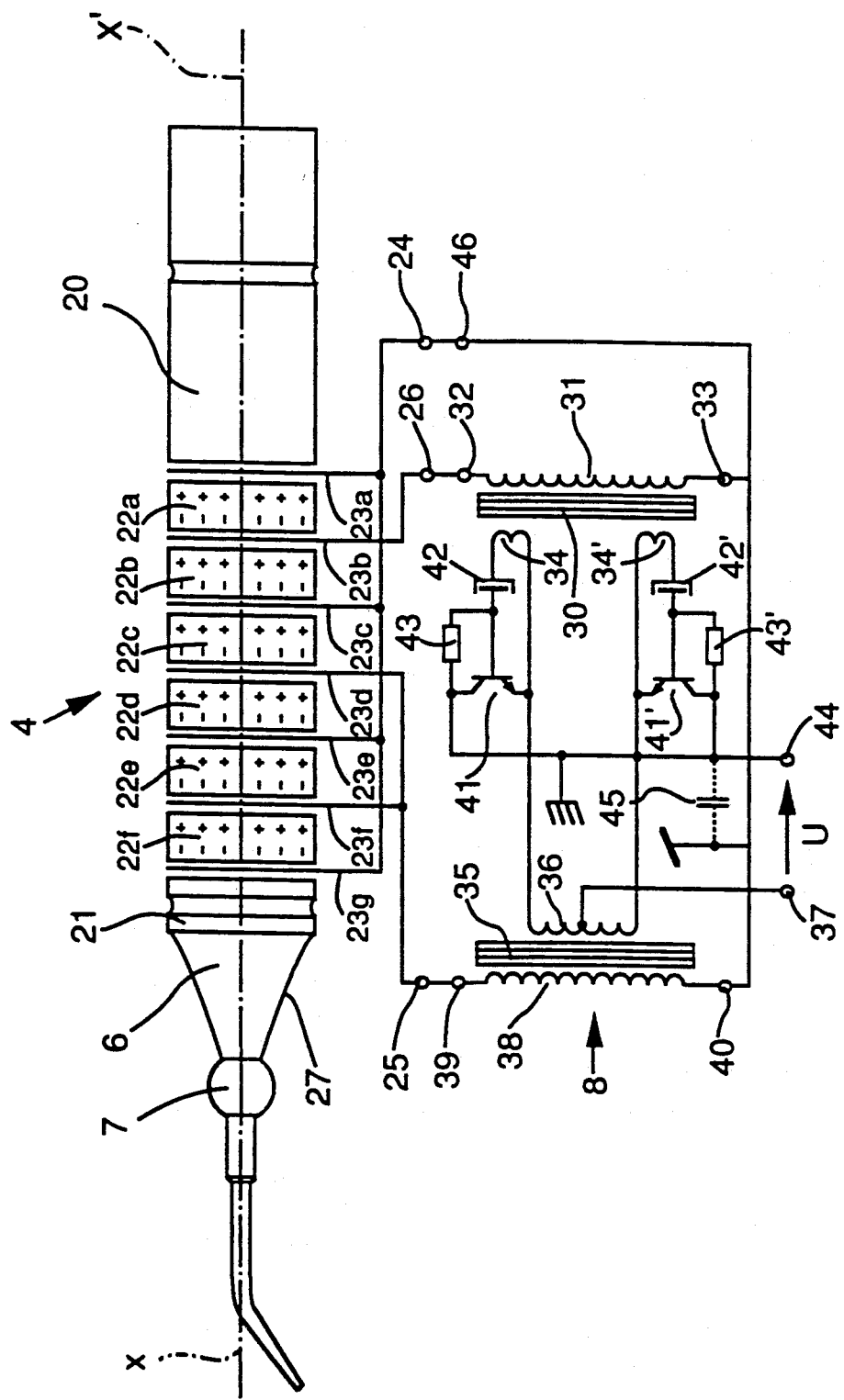
FIG. 3 is a schematic diagram showing the transducer with its electrodes, the scraper, and the circuit of the amplifier to which the electrodes are connected.

Transducer 4, shown in detail in FIG. 3, includes a base 20, a head 21, six piezoelectric chips 22a through 22f, and seven electrodes 23a through 23g.

The base 20 is a metal cylinder whose axis of symmetry is the axis xx'. The dimensions of the base 20 are chosen in such a manner, that of the total mass of the transducer 4, the base will be preponderant. The base thus displays a great deal of inertia. The result of this is that when the transducer vibrates, the base remains practically immobile and thus constitutes a node of motion of the transducer.

The piezoelectric chips 22a . . . 22f are identical flat, cylindrical disks. Each chip is cut in the piezoelectric material in such a manner that a constraint in axial pressure will cause positive charges to appear on one of its main surfaces, and negative charges on the other surface. The chips 22a . . . 22f are aligned along axis xx', one after the other, with chip 22a being opposite the base 20. Additionally, the chips are turned in such a manner that the adjacent main surfaces carry a charge of the same sign, when these chips are subjected to an axial constraint. The head 21 is applied against the free main surface of chip 22f, and includes a metallic disk of cylindrical shape and has a mass smaller than that of the base 20. Lastly, the electrodes 23a . . . 23g are arranged facing the main surfaces of chips 22a . . . 22f. The electrode 23a is thus placed between the base 20 and the chip 22a, electrode 23b between chips 22a and 22b, etc., and electrode 23g between chip 22f and head 21.

To make FIG. 3 clearer, space has been arranged on each side of chips 22a . . . 22f, with one of the electrodes 23a . . . 23g arranged in each of these spaces. In reality, the chips and the electrodes are squeezed in between the base 20 and the head 21 so as to be in contact with each other. Thus, all this forms a block of different components which are held together by gluing and by means of a center screw, not shown, joining the base to the head.

The electrodes 23a, 23c, 23e and 23g, that is, all the odd electrodes as counted from one of the extremities of the transducer, are connected to a mass terminal 24 of the transducer 4. The electrodes 23d and 23f, i.e., the even electrodes, except for the second electrode as counted from base 20, are connected to an input terminal 55. Lastly, the second electrode 23b is connected to an output terminal 26. Terminals 25 and 24 form the input of the transducer and terminals 26 and 24 its output.

Application of an alternating voltage between terminals 25 and 24 causes the vibration of the transducer at the frequency of this voltage. Voltage of the same frequency then appears between terminals 26 and 24, the amplitude of this voltage being proportional to the amplitude of vibration.

With the base 20 of the transducer being practically at rest, the chip 22f and the head 21 vibrate at the greatest amplitude and thus constitute an antinode of motion of the transducer. When the frequency of the voltage applied between terminals 25 and 24 is equal to the basic resonant frequency of the transducer connected to the scraper, the amplitude of motion of the head reaches a maximum. To ensure that this amplitude corresponds to the optimum operating conditions of the scaler, the voltage must be on the order of 600 volts.

The scraper 2 may be attached directly at the right side of the antinode of motion of the transducer, its amplitude of vibration then being identical to that of head 21. However, in order to improve on the effectiveness of the scraper, it is advantageous to amplify its motion in relation to that of the head. This is achieved in this invention by connecting the scraper 2 to the head 21 by means of a coupling means consisting of a weight 7 holding the scraper and an elastic connecting means 6 arranged between the weight and the head. The weight with the scraper and the connecting means 6 form a vibrating system. By tuning the resonant frequency of this system to a frequency that is essentially equal to the frequency of vibration of the head, and if the mass of the weight and of the scraper is smaller than that of the active extremity of the transducer, the amplitude of motion of the scraper will be greater than that of the head. The weight 7 will advantageously have a spherical shape and the connecting means 6 will have that of a rotating body generated by an exponential curve 27 turning around the axis xx', with the part having the thickest section of the connecting unit being on the side of the head 21. The head 21, the weight 7 and the connecting means 6 will preferably be executed in such a manner as to form a single metal part.

The input voltage of transducer 4 is supplied by amplifier 8 shown in FIG. 3. The reference 30 in this figure indicates a stepdown transformer with a primary (winding) 31, having two terminals 32 and 33, and a secondary formed by two identical windings 34 and 34', with the ratio between the number of turns of the primary and of one of the secondary windings being on the order of 1000. Similarly, the reference 35 designates a step-up transformer having a primary 36 provided with a center tap connected to the terminal 37, and a secondary having two terminals, 39 and 40, with the ratio between the number of turns of the primary and the secondary being 1/10. Terminals 33 and 40 are connected to a terminal 46 constituting the electric mass of amplifier 8 the input of which is formed by terminals 32 and 46, and the output by terminals 39 and 46.

A power amplifier, known from prior art and consisting of two symmetrical parts, is connected between the secondary of transformer 30 and the primary of transformer 35. In one of said parts, a bipolar transistor 41, type NPN, has its emitter connected to one of the terminals of winding 34 and to one of the terminals of winding 36. The base of this transistor is connected through a condenser 42 of approximately 6 microfarads to the other terminal of winding 34. Lastly, a polarization resistance 43 of about 2000 ohms connects the base to the collector of transistor 41, the collector in turn being connected to a terminal 44. The other part of the circuit consists of the elements 41', 42' and 43', which are identical to elements 41, 42 and 43, respectively, and which are connected in the same manner as the latter, but between the winding 34' and the other terminal of winding 36. The terminals 37 and 44 constitute the feeder terminals of the circuit and they are connected, respectively, to conductors 9 and 10 of the universal connector.

Since the signals at the terminals of the windings between which the amplifier circuit is connected have low amplitudes, the circuit may be fed by direct low voltage.

The collectors of transistor 41 and 41' being connected to terminals 44, it is advantageous to connect this terminal to the mass of sleeve 1, which also constitutes the mass of the device. In effect, as in a power transistor, the collector is integral with a massive electrode serve to evacuate the heat, which arrangement permits attaching the electrode directly on sleeve 1 to further improve the cooling of the transistor. Terminals 46 and 44 correspond, respectively, to the electric mass and the mass of the device, and can be independent, joined galvanically or, preferably, connected together by a decoupling condenser 45 of about 0.1 microfarad.

The transducer 4 is connected to the amplifier 8 to form an oscillator, with the transducer coupled to scraper 2 playing the role of resonator and the amplifier that of the maintenance circuit. The connection is effected by connecting the terminals 24, 25 and 26 to terminals 46, 39 and 32, respectively. Application of a U-type direct current feeder voltage, typically of 24 volts, supplied by the energy source and rendering terminal 44 positive in relation to terminal 37, will cause the start of the oscillator, if the amplifier gain compensates for the losses of the transducer, with the amplitude of oscillation depending on the value of the U-voltage.

The dental scaler described above can, of course, be subject to various modifications and may be a form of other variants that are evident to the expert, without departing from the scope of this invention.

The transducer could comprise a different number of piezoelectric chips and the electrodes could be connected to each other in such a manner as to present only two terminals. The amplifier could, for example, form with the transducer, when the latter has only two terminals, a Colpitts oscillator.

While specific embodiments of the invention have been shown and described in detail to illustrate the application of the principles of the invention, it will be understood that the invention may be embodied otherwise without departing from such principles.

I claim:

1. A dental scaler comprising an oblong hollow sleeve that can be held by hand, and arranged inside the sleeve the scaler comprising:
   a vibrating piezoelectric transducer having a first extremity as a base, a second extremity as a head, an electric input, and an electric output, said extremities being disposed along a longitudinal axis of the sleeve;
   a scraper secured to said transducer by coupling means and having a member protruding from said sleeve, said coupling means having an elastic connecting means fixed to said transducer at an antinode of displacement and a weight attached to said elastic connecting means and bearing said scraper, said weight and said scraper forming with the said elastic connecting means a vibrating system having a resonant frequency essentially equal to a frequency of vibration of said transducer; and
   an electronic amplifier having an amplifier input, an amplifier output and two feeder terminals, said feeder terminals receiving, from an external power supply, energy necessary for operation of the scaler, said amplifier input and said amplifier output being connected respectively to said transducer output and said transducer input so as to form an oscillator, said amplifier acting as a sustaining circuit and said transducer as a resonator vibrating along said longitudinal axis, said base and said head being respectively at a node and at an antinode of displacement of said transducer.

2. Scaler according to claim 1, wherein:
   said elastic connecting means is fixed on said head of said transducer.

3. Scaler according to claim 1, wherein:
   said elastic connecting means and said weight have a shape of a body formed by revolution about an axis, said axis of revolution coinciding with said longitudinal axis of the sleeve.

4. Scaler according to claim 3, wherein:
   said elastic connecting means is generated by an exponential curve, a thick section of said elastic connecting means being fixed to said head.

5. Scaler according to claim 1, wherein:
   a mass of said weight is smaller than a mass of said head, causing an amplitude of displacement of said weight and said scraper, at said resonant frequency to be greater than an amplitude of displacement of said head.

6. Scaler according to claim 1, wherein:
said weight, said head and said elastic connecting means constitute a single piece.

7. A dental scaler comprising:
a vibrating transducer having a first extremity and a second extremity;
a base attached to said first extremity of said vibrating transducer holding said first extremity substantially immobile;
an elastic connecting means attached to said second extremity of said transducer, said elastic connecting means having securing means for holding one of a tool or said tool and a weight, said elastic connecting means forming a vibrating system with one of said tool or said tool and said weight, said vibrating system having a resonant frequency substantially similar to a resident frequency of said vibrating transducer; and
an electric amplifier circuit to drive said vibrating transducer at said resonant frequency.

8. A scaler in accordance with claim 7, wherein:
said connecting means with one of said tool or said tool and said weight forming said vibrating system with an amplitude of displacement at said tool greater than an amplitude of displacement at said second extremity of said transducer.

* * * * *